United States Patent [19]

Häkkinen

[11] 4,276,876
[45] Jul. 7, 1981

[54] RESPIRATOR APPARATUS

[76] Inventor: Taisto Häkkinen, Kaarlonkatu 25, 13210 Hämeenlinna 21, Finland

[21] Appl. No.: 30,843

[22] Filed: Apr. 17, 1979

[30] Foreign Application Priority Data

Apr. 18, 1978 [FI] Finland ................................ 781170

[51] Int. Cl.³ .............................................. A61M 11/00
[52] U.S. Cl. ........................... 128/200.14; 128/200.21; 128/204.25; 128/205.24
[58] Field of Search ...................... 128/200.14, 200.15, 128/200.16, 200.17, 200.18, 200.21, 200.22, 203.25, 203.28, 203.29, 204.25

[56] References Cited

U.S. PATENT DOCUMENTS

| | | | |
|---|---|---|---|
| 3,083,707 | 4/1963 | Seeler | 128/204.27 X |
| 3,234,932 | 2/1966 | Bird et al. | 128/204.25 |
| 3,584,621 | 6/1971 | Bird | 128/200.18 |
| 3,667,463 | 6/1972 | Barnes | 128/200.14 |
| 3,720,207 | 3/1973 | Matheny et al. | 128/205.25 X |
| 3,903,884 | 9/1975 | Huston et al. | 128/200.18 |

FOREIGN PATENT DOCUMENTS 1187461  4/1970  United Kingdom ................ 128/200.21

Primary Examiner—Henry J. Recla
Attorney, Agent, or Firm—Steinberg & Raskin

[57] ABSTRACT

Respirator apparatus for assisting in the respiration of a patient who is indisposed or whose lungs are damaged includes a modular system to which various components may be added so that the same apparatus can be modified for various purposes. The respirator apparatus is a modular system comprising a basic unit, namely a drug atomizer and a control valve associated therewith which regulates the flow of air or oxygen to the drug atomizer. A flexible tube is fluidly coupled between a connector provided on the control valve and a pressure supply source. Associated with this modular system are a respiration pressure control valve which is connected to the drug atomizer control valve, an injector member fluidly connected to the drug atomizer, a flexible tube fluidly intercommunicating the respiration pressure control valve and the other end of the injector member and an expiration valve mounted between the respirator mouthpiece and the drug atomizer by which the counter-pressure presented during expiration can be steplessly adjusted.

8 Claims, 4 Drawing Figures

RESPIRATOR APPARATUS

BACKGROUND OF THE INVENTION

This invention relates generally to respirator apparatus and, more particularly, to respirator apparatus which can be modified for applications other than that of a conventional respirator.

Respirators of the type which provide for the inhalation of medicated vapors or of gases by the patient are well known. Such respirators are generally used in connection with assisting in the respiration of persons afflicted with damaged or diseased lungs whose respiration is thus impaired.

Generally, respirators are provided with drug atomizers which atomize a medicinal agent to facilitate its administration by the patient's inspiration together with compressed air or the like, deeply into even the smallest bronchi.

One type of such respirator is disclosed in applicant's Finnish patent application No. 753,748, which respirator includes as one component thereof an expiration valve whereby the counterpressure presented to the patient's expiration can be adjusted in a stepless or continuous manner. This respirator is suitable for use in various applications such, for example, as in hospital use, home use, water safety use, such as at beaches and swimming pools, in vehicles and in various transport applications.

However, such respirators of the type disclosed in the above-identified Finnish patent application, are not entirely satisfactory. More particularly, such respirators generally comprise an integral apparatus which cannot be modified for applications for which the respirator was not originally intended. Automatic respirators which are generally used in hospitals and the like are subject to the same disadvantage. Further, such integrally formed automatic respirators are generally expensive in manufacture.

SUMMARY OF THE INVENTION

Accordingly, one object of the present invention is to provide a new and improved respirator apparatus.

Another object of the present invention is to provide a new and improved respirator apparatus comprising a modular system which may be constructed in a simple and rapid manner so as to be suitable for various applications.

Yet another object of the present invention is to provide a new and improved respirator apparatus which is inexpensive in manufacture and operation.

Briefly, in accordance with the present invention, these and other objects are attained by providing a respirator apparatus comprising a modular system including a basic unit, namely a drug atomizer provided with a control valve for regulating the flow of air or oxygen to the drug atomizer. The control valve is fitted with an entrance connector to which one end of a flexible tube is fluidly connected and whose other end is adapted to be fluidly coupled to a pressurized source of air, oxygen or the like.

The modular system described above is adapted to have various components connected thereto in a quick and easy manner so as to provide a respirator suitable for a variety of uses. More particularly, a respiration pressure control valve is connected to the drug atomizer control valve and an injector member has one of its ends connected to the drug atomizer. A flexible tube has one of its ends fluidly coupled to the respiration pressure control valve and its other end fluidly coupled to the other end of the injector member. An expiration valve, preferably of the type whereby the counter-pressure presented during expiration by the patient can be steplessly or continuously adjusted, is mounted between a mouthpiece and the drug atomizer.

In this manner, a modular system is provided having a simple basic construction to which additional components are easily associated for providing a respirator apparatus which is suitable for various applications. The construction of the respirator apparatus is extremely simple and may be achieved in a minimum amount of time at minimum cost. The components of the respirator apparatus may be utilized or omitted according to the particular application for which the apparatus is intended thereby providing a versatility not otherwise obtainable with conventional respirator apparatus.

DESCRIPTION OF THE DRAWINGS

A more complete appreciation of the invention and many of the attendant advantages thereof will be readily appreciated as the same becomes better understood by reference to the following detailed description when considered in connection with the accompanying drawings in which.

DESCRIPTION OF THE PREFERRED EMBODIMENTS

Figure 1:
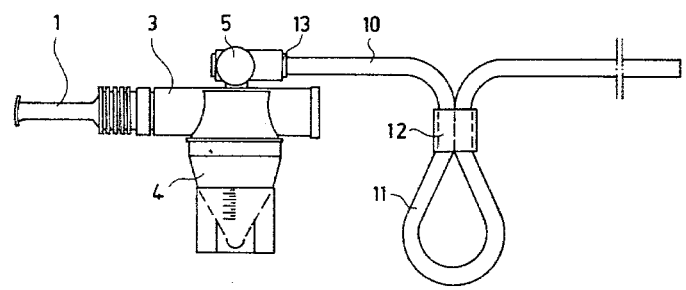
FIG. 1 is a schematic elevation view of a modular system according to the present invention.

Referring now to the drawings wherein like reference characters designate identical or corresponding parts throughout the several views, and more particularly FIG. 1, the modular system of the present invention is illustrated and includes a basic unit, namely a drug atomizer 3 to which is connected a drug atomizer control valve 5 by means of a suitable connector, such as conical connector. The drug atomizer control valve 5 serves to regulate the rate of flow of air or oxygen into the drug atomizer 3. The atomizer control valve 5 is provided with a suitable connector 13 to which one end of a flexible tube is attached for connecting the valve 5 to a source of pressurized air or oxygen to facilitate the atomization of the medicinal agent in the drug atomizer 3. The medicinal agent is contained within the receptacle 4 attached to the drug atomizer 3 as illustrated in FIG. 1. A conventional mouthpiece 1 has one end thereof fluidly connected to the drug atomizer 3, its free end being adapted to be placed within the mouth of the patient.

The modular system illustrated in FIG. 1 further includes a flexible tube 10 constructed so as to withstand an elevated internal gaseous pressure. One end of the tube 10 is fluidly coupled to the connector 13 of the control valve 5 while the other end thereof is adapted to be connected to a source of pressurized air, oxygen or the like. More particularly, the drug atomizer 3 is supplied with pressurized air or oxygen through the regulating control valve 5, the latter being connected through the pressure tube 10 to a source of pressurized air or oxygen. The compressed air or oxygen serves to atomize the medicinal agent contained within the receptacle 4 for inhalation through mouthpiece 1 by the patient.

Figure 3:
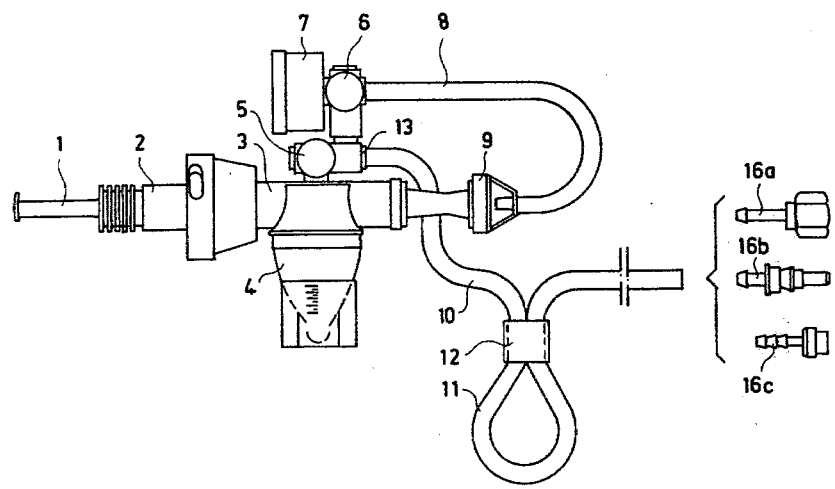
FIG. 3 is a schematic elevation view of a respirator according to the present invention which has been constructed in the manner illustrated in FIG. 2.

The pressure supply for the drug atomizer 3, i.e., the compressed or pressurized air or oxygen, may advantageously be obtained from any one of a number of sources. Thus, as schematically illustrated in FIG. 3, the free end of pressure tube 10 may be connected to the reducing valve of an oxygen flask or compressor, designated by the connection 16a. Alternatively, the pressure tube 10 may be connected to a wall outlet for the supply of oxygen or compressed air, schematically designated by the connection 16b in FIG. 3, typically found in hospitals. Still further, in an emergency, the free end of pressure tube 10 may be coupled to the valve of an automobile tire, designed 16c in FIG. 3, which has been found sufficient to provide the supply pressure for the drug atomizer.

The pressure tube 10 of the modular system illustrated in FIG. 1 is preferably formed in the shape of a loop 11 for the purpose of regulating the flow of air or oxygen into the drug atomizer 3 during expiration of the patient. More particularly, by urging the opposed side portions of pressure tube 10 defined by loop 11 towards each other, the flow of the compressed gas through the tube can be inhibited. By so inhibiting the flow of air or oxygen into the drug atmoizer 3 during expiration by the patient, consumption of the medicinal agent as well as the oxygen can be reduced up to 50% since during the patient's exhalation, no air or oxygen can be introduced into the drug dispenser without the medicinal agent flowing from the atomizer 3 during exhalation. A sleeve 12 is preferably utilized through which the pressure tube 10 is passed in two directions in order to define the loop 11. By sliding the sleeve 12 over the length of the tube 10, the size of loop 11 may be selectively increased or decreased or, in fact, closed completely. In other words, as will be understood by those skilled in the art, when the sleeve 12 is moved downwardly (as seen in FIG. 1), the size of the loop decreases or closes thereby reducing the effective fluid transmitting cross-section thereof so that the flow rate of pressurized oxygen or air is reduced. When the sleeve 12 is moved downwardly to the maximum extent possible so that the loop is closed, i.e., has its minimum diameter, the walls of the tube will be crimped thereby effectively cutting off the fluid flow completely. In this manner, the flow of pressurized oxygen or air through the pressure tube 10 into the drug atomizer 3 may be rapidly and easily reduced or even terminated by moving the sleeve 12 to completely close the loop 11.

Figure 2:
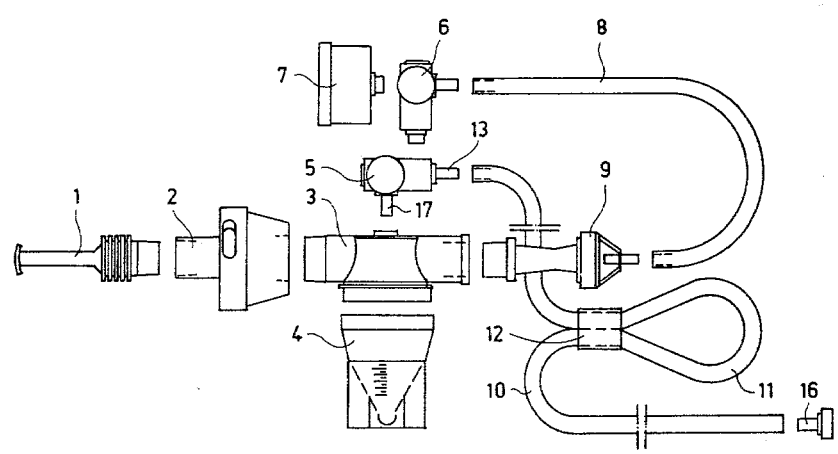
FIG. 2 is a schematic elevation view illustrating the modular system of FIG. 1 in disassembled form together with additional components, also in disassembled form, which are associated with the modular system to form a respirator according to the present invention.

Referring now to FIG. 2, the modular system illustrated in FIG. 1 is shown in an exploded view to facilitate the understanding of its construction and, further, illustrates the association of additional components, also in an exploded fashion, whereby the modular system is supplemented to comprise a respirator according to the present invention. More particularly, an expiration or exhalation valve 2 is located between the drug atomizer 3 and the mouthpiece 1. The expiration valve 2 is preferably of the type wherein the counter-pressure presented during patient exhalation can be adjusted in a stepless or continuous manner. Such an expiration valve is disclosed in applicant's copending patent application filed simultaneously herewith.

A respiration pressure control valve 6 equipped with a pressure gauge 7 is connected to the drug atomizer control valve 5 which serves to regulate the respiration pressure at which the respirator of the present invention operates.

An injector member 9 has its outlet end connected to the drug atomizer 3 as shown in FIGS. 2 and 3. A flexible pressure tube 8 has its ends connected to the respiration pressure control valve 6 and the inlet end of the injector member 9, respectively.

Thus, referring to FIGS. 1-3, it is seen that a modular system (FIG. 1) is provided to which various components may be selectively added in a simple and rapid manner to obtain a respirator which is suitable for many diverse applications. As clearly shown in FIG. 2, each individual component of the respirator is adapted to be quickly interconnected with the other components thereof. Additionally, various components may be omitted as desired. Thus, for example, the expiration valve 2 may be omitted entirely, as discussed below, with the mouthpiece 1 being directly connected to the drug atomizer 3.

In operation, referring to FIG. 3, the pressure tube 10 is connected to suitable source of pressurized oxygen or air to provide the supply pressure for the drug atomizer 3. Where the respirator is used in a hospital environment, the free end of pressure tube 10 is connected to connector 16b which, as mentioned above, designates an oxygen or compressed air wall outlet typically found in hospitals. The output of the atomized medicinal agent from the drug atomizer 3 is adjusted through suitable adjustment of the drug atomizer control valve 5. Similarly, the respiration pressure offerred by the respirator is regulated as desired by suitably adjusting the respiration pressure control valve 6. As will be readily understood by those having skill in the art, the oxygen content of the air inspired by the patient can be obtained from known tables which correspond to the particular respirator construction taking into account the position to which the drug atomizer control valve 5 is set as well as the respiration pressure which, of course, is indicated by the pressure gauge 7.

Figure 4:
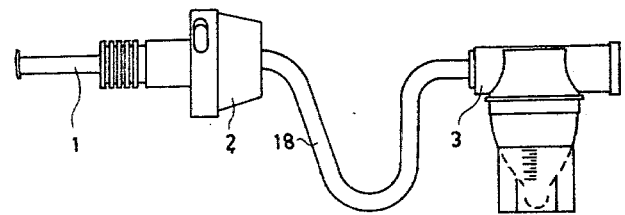
FIG. 4 is a schematic elevation view of a modification of a respirator apparatus illustrated in FIG. 3 according to the present invention.

The counter-pressure to the patient's expiration presented by the respirator is regulated by means of the expiration valve 2. Preferably, expiration valve 2 is of the type which is capable of adjusting the counter-pressure in a stepless or continuous manner. Thus, for example, the expiration valve 2 may be of the type disclosed in applicant's copending patent application, filed simultaneously herewith which includes an adjusting ring which can be moved to adjust the extent of the counter-pressure. The expiration valve essentially comprises a pair of interconnected members having a diaphragm mounted therebetween which is axially acted upon from the direction of the drug atomizer 3 by a force exerted by the pressurized gas within the atomizer whereby the diaphragm will open. However, when the pressurized flow ceases during expiration (with the pressure flow through pressure tube 10 being inhibited in the manner set forth above) the diaphargm will close. The exhalation will pass through the aperture in the adjustment ring so that the latter enables the counter-pressure to exhalation to be steplessly or continuously adjusted.

Where the respirator of the present invention is installed in a manner such that is cannot be readily moved, and where the patient is located at a distance from the respirator, the expiration valve 2 can be readily connected to the drug atomizer 3 by means of a flexible tube 18, as seen in FIG. 4. Thus, particularly in situations where the patient is incapacitated or is weak and must remain in a prone position, the mouthpiece 1 and associated expiration valve 2 may be associated with the drug atomizer 3 in a manner such that it may be freely moved relative thereto so that the mouthpiece 1 affixed to the expiration valve 2 may be guided into the patient's mouth with accuracy and ease.

As mentioned above, the apparatus of the present invention is advantageous in that it allows for modifications to be made therein so that the resulting apparatus may be used in connection with various applications. Thus, the respirator apparatus of the present invention, as illustrated in FIG. 3 or as modified according to the embodiment illustrated in FIG. 4, may also be used as a so-called bronchoscopy anaesthetic apparatus, by means of which an anaesthetic fluid can be directed into the patient's lungs. Further, in applications such as anaesthetic use, the expiration valve 2 may be unnecessary and, in such cases, the respirator illustrated in FIG. 3 may be easily converted into a bronchoscopy anaesthetizer by simply removing the expiration valve 2 from between the mouthpiece 1 and the drug atomizer 3 and inserting the mouthpiece end directed into the drug atomizer.

Thus, the present invention provides respirator apparatus which may be modified according to its intended use in a simple and quick manner. This is made possible through the provision of an modular system comprising a drug atomizer and associated control valve, the latter components comprising a basic unit, and a flexible pressure tube. Additional components such, for example, as the expiration valve, a respiration pressure control valve, etc., are easily adapted for connection to the modular unit in the manner set forth above.

Obviously, numerous modifications and variations of the present invention are possible in the light of the above teachings. It is therefore to be understood that within the scope of the appended claims, the invention may be practices otherwise than is specifically recited herein.

What is claimed is:

1. Modular respirator system apparatus for assisting in the respiration of a patient who, for example, is indisposed, unconscious or whose lungs are damaged or otherwise diseased, comprising:
    a basic assembly comprising drug atomizing means having an outlet and atomizer control valve means attached to said drug atomizing means for regulating a flow of oxygen or air into said drug atomizing means, said atomizer control valve means having an entrance connector fitting provided thereon for conducting air or oxygen into said control valve means, and a first flexible tubular connector having one end attached to said entrance connector fitting of said atomizer control valve means and the other end adapted to be connected to a pressure supply source;
    valve means for controlling respiration pressure detachably connected to said atomizer control valve means of said modular system, said respiration pressure control valve means including pressure gauge means for monitoring the respiration pressure at which the respirator operates;
    means for detachably connecting said respiration pressure control valve means to said atomizer control valve means so that the former can be selectively connected to or detached from the latter;
    an injector member one end of which is detachably connected to said drug atomizing means of said modular system;
    a second flexible tubular connector which, when said respiration pressure control valve means and injector member are connected to said atomizer control valve means and said drug atomizing means of said modular system, respectively, has one end fluidly coupled to said respiration pressure control valve means and its other end fluidly coupled to the other end of said injector member;
    expiration valve means for steplessly adjusting the counter-pressure presented to the patient's expiration, said expiration valve means being fluidly detachably connectable between the outlet of said drug atomizing means and a mouthpiece; and
    a mouthpiece having one end fluidly detachably connected to said expiration valve means.

2. Respirator apparatus as recited in claim 1 further including a third flexible tubular connector having one end fluidly connected to said expiration valve means and the other end fluidly connected to the drug atomizing means.

3. Respirator apparatus as recited in claim 1 wherein said first flexible tubular connector has a loop formed therein defining a pair of opposed loop portions, and means for varying the size of the loop to thereby reduce or enlarge the flow passage through the first flexible tubular element to inhibit the flow of air or oxygen into the drug atomizing means during expiration by the patient.

4. Respirator apparatus as recited in claim 3 wherein said loop size varying means comprises a sleeve member slidably disposed on said first flexible tubular connector in a manner such that the size of said loop may be enlarged or reduced by sliding said sleeve thereover so that the flow of air or oxygen through said first flexible tubular element can be selectively inhibited or terminated.

5. Respirator apparatus as recited in claim 1 wherein said other end of said first flexible tubular connector is connectable to a reducing valve of an oxygen flask or compressor.

6. Respirator apparatus as recited in claim 1 wherein said other end of said first flexible tubular connector is connectable to an outlet of a hospital's oxygen or compressed air system.

7. Respirator apparatus as recited in claim 1 wherein said other end of said flexible tubular connector is adapted to be connectable to a valve of an automobile tire.

8. Modular respirator system apparatus for assisting in the respiration of a patient who, for example, is indisposed, unconscious or whose lungs are damaged or otherwise diseased, comprising:
    a basic assembly comprising drug atomizing means and atomizer control valve means attached to said drug atomizing means for regulating a flow of oxygen or air into said drug atomizing means, said atomizer control valve means having an entrance connector fitting provided thereon for conducting air or oxygen into said control valve means, and a first flexible tubular connector having one end attached to said entrance connector fitting of said atomizer control valve means and the other end adapted to be connected to a pressure supply source;

valve means for controlling respiration pressure detachably connected to said atomizer control valve means of said modular system, said respiration pressure control valve means including pressure gauge means for monitoring the respiration pressure at which the respirator operates;

means for detachably connecting said respiration pressure control valve means to said atomizer control valve means so that the former can be selectively connected to or detached from the latter;

an injector member one end of which is detachably connected to said drug atomizing means of said modular system;

a second flexible tubular connector which, when said respiration pressure control valve means and injector member are connected to said atomizer control valve means and said drug atomizing means of said modular system, respectively, has one end fluidly coupled to said respiration pressure control valve means and its other end fluidly coupled to the other end of said injector member; and a mouthpiece having one end fluidly detachably connected to said drug atomizing means.

* * * * *